United States Patent [19]

Orth

[11] Patent Number: 5,380,302
[45] Date of Patent: Jan. 10, 1995

[54] CANNULA FIXATION DEVICE WITH RETAINING RING HAVING IDENTATIONS

[75] Inventor: Michael J. Orth, San Jose, Santa Clara County, Calif.

[73] Assignee: Unisurge, Inc., Cupertino, Calif.

[21] Appl. No.: 16,072

[22] Filed: Feb. 10, 1993

[51] Int. Cl.⁶ .............................................. A61M 25/00
[52] U.S. Cl. ..................................... 604/283; 604/164
[58] Field of Search ............... 604/283, 905, 174, 178, 604/177, 164, 158, 169, 264, 268, 256, 240–243, 272, 273, 239; 606/108; 128/DIG. 26, 912

[56] References Cited

U.S. PATENT DOCUMENTS

| | | | |
|---|---|---|---|
| 3,540,451 | 11/1970 | Zeman | 604/27 |
| 3,957,048 | 5/1976 | Jacobs | 604/180 |
| 4,252,122 | 2/1981 | Halvorsen | 604/164 |
| 4,786,281 | 11/1988 | Valentini et al. | 604/256 |
| 5,176,648 | 1/1993 | Holmes et al. | 604/164 |
| 5,232,440 | 8/1993 | Wilk | 604/49 |
| 5,257,973 | 11/1993 | Villasuso | 604/49 |

Primary Examiner—C. Fred Rosenbaum
Assistant Examiner—V. Alexander
Attorney, Agent, or Firm—Flehr, Hohbach, Test, Albritton & Herbert

[57] ABSTRACT

A retaining ring comprising a body of elastomeric material. The body has a wall with a generally cylindrical configuration and a longitudinal axis. The body also has an outer cylindrical surface and first and second end surfaces. The body has a bore extending therethrough along the longitudinal axis and through the first and second end surfaces with the wall of the body defining the bore. A plurality of circumferentially spaced-apart indentations are formed in the wall of the body and extend outwardly through the outer surface between the first and second ends.

11 Claims, 1 Drawing Sheet

CANNULA FIXATION DEVICE WITH RETAINING RING HAVING IDENTATIONS

This invention relates to a cannula fixation device with retaining ring having indentations therein for use with an introducer assembly that is used for introducing a cannula into a body cavity of a patient.

Introducer assemblies have heretofore been provided, as for example as described in U.S. Pat. No. 5,176,648. Gaskets or retaining rings have heretofore been provided in such assemblies for gripping the cannula to hold it in a fixed position. However, it has been found that it is difficult to obtain a good gripping with such retaining rings because it has been found that the outside diameters of cannulas can vary appreciably. As for example a 5 millimeter cannula can vary in outside diameter by 1 to 1-½ millimeters which is approximately 0.040-0.060 inches. In addition, it has been found with cannulas varying this much in the outside diameter it has been difficult to fix the cannulas in a predetermined position with respect to the retaining ring. There is therefore need for a new and improved retaining ring which can be utilized in a cannula fixation device to overcome these deficiencies.

In general, it is an object of the present invention to provide a cannula fixation device which can be utilized in an introducer assembly and which can accommodate a relatively large variation in sizes with respect to the outside diameters of cannulas being introduced therethrough.

Another object of the invention is to provide a cannula fixation device of the above character which includes a retaining ring which is capable of a large clamping range under low compressive loads.

Another object of the invention is to provide a cannula fixation device of the above character in which the large clamping range for the retaining ring can be obtained without sacrificing the continuous edge on either end of the retaining ring.

Another object of the invention is to provide a cannula fixation device of the above character in which the retaining ring is capable of readily returning to its original shape when the compressive load is removed.

Another object of the invention is to provide a cannula fixation device of the above character in which the cannula will not catch when it is introduced through the device.

Another object of the invention is to provide a cannula fixation device in which the retaining ring is relatively insensitive to durometer and material selection.

Additional objects and features of the invention will appear from the following description which the preferred embodiment is set forth in detail in conjunction with the accompanying drawings.

In general, the cannula fixation device is for use with an introducer assembly which is utilized for introducing a cannula into a body cavity of a patient having a skin overlying the cavity. It comprises a retaining ring having a bore extending therethrough which is adapted to receive the cannula and a locking member for compressing the retaining ring so as to engage said cannula to retain the cannula in a fixed position. The retaining ring is formed of a body of elastomeric material and has a generally cylindrical configuration with an outer cylindrical surface and the first and second end surfaces through which the bore extends. A plurality of circumferentially spaced-apart indentations are formed in the body and extend longitudinally and outwardly of the body through the outer surface between the first and second ends.

Figure 2:
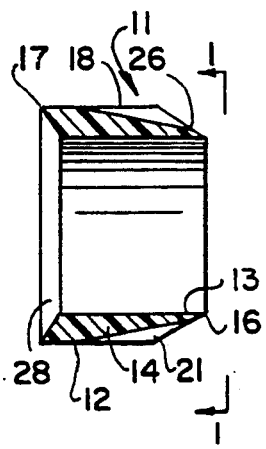
FIG. 2 is a cross-sectional view taken along the line 2—2 of FIG. 1.
Figure 1:
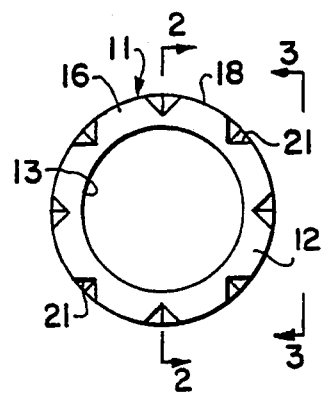
FIG. 1 is a top end view looking along the line 1—1 of FIG. 2 of a retaining ring incorporating the present invention.
Figure 3:
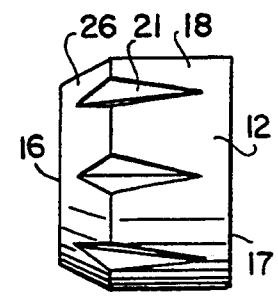
FIG. 3 is a side-elevational view looking along the line 3—3 of FIG. 1.

More in particular, the retaining ring 11 incorporating in the present invention consists of a body 12 of an elastomeric material of a suitable type such as Santoprene, 55 durometer Shore A, Advanced Elastomer 281–55. It should be appreciated, however, that other durometers can be used. Different materials can be utilized such as Silicon, Kraton, and polyethylene. The body 12 is generally cylindrical in shape as shown in FIGS. 1-3 and is provided with an axially extending bore 13 formed by a wall 14 which extends through first and second end surfaces 16 and 17 which are generally planar and parallel to each other. The body is also provided with a cylindrical outer surface 18 which extends perpendicular to the first and second end surfaces 16 and 17.

A plurality of circumferentially spaced-apart indentations 21 are provided in the body and extend in an axial direction of the body longitudinally of the body. The indentations extend outwardly through the outer surface 18 between the first and second ends 16 and 17. The indentations 21 are substantially V-shaped in the cross section and have a slope of decreasing depth in a direction from the first surface to the second surface. The 9° angle is defined by the height of the device and the need for the indentations 21 to exit the outer surface 18 and that angled surface 26. The V-shaped indentations 21 can have a suitable included angle, as for example of 90°. A suitable number of indentations as for example, eight as shown in the drawings can be provided which are equally spaced-apart circumferentially.

The body 12 is also formed with an inclined annular surface 26 which extends downwardly and outwardly from the first surface 16. The inclined surface 26 is inclined at a suitable angle ranging from 25° to 55°, as for example 29°. Another inclined annular surface 28 is formed on the body 12 and extends inwardly and upwardly from the second end surface 17. The surface 28 can extend at a suitable angle ranging 30° to 60°, as for example 55°.

Figure 4:
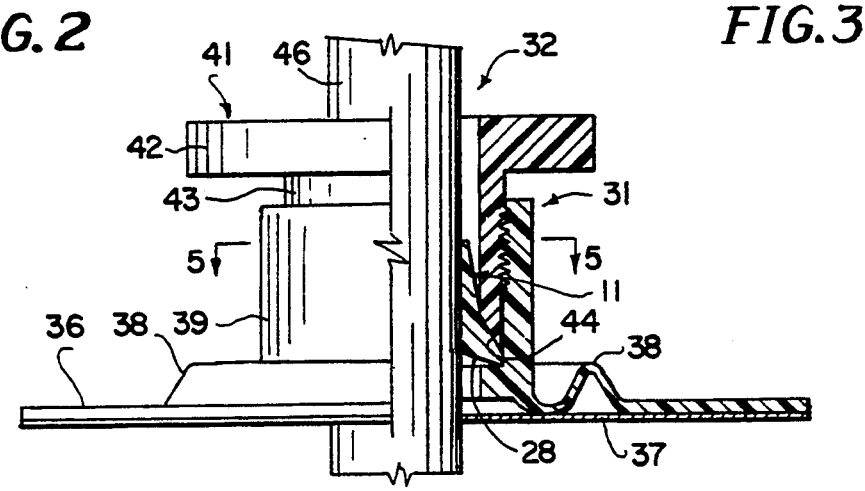
FIG. 4 is a side elevational view partially in cross-section of an introducer assembly which incorporates the cannula fixation device of the present invention.
Figure 5:
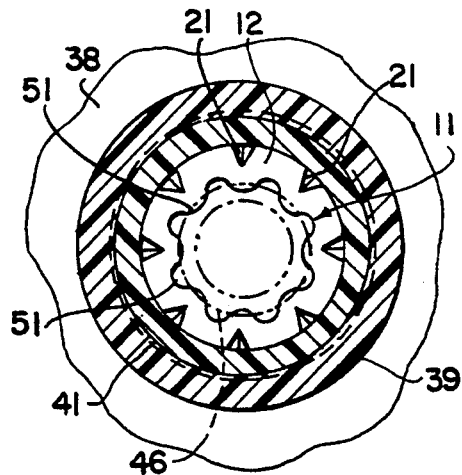
FIG. 5 is a cross-sectional view of taken along the line 5—5 of FIG. 4 with the retaining ring partially compressed.
Figure 6:
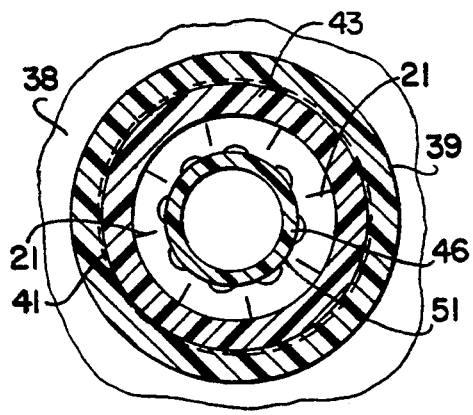
FIG. 6 is a cross-sectional view similar to FIG. 5 showing the retaining ring in a substantially fully compressed condition.

The retaining ring 11 hereinbefore described is adapted for use in a fixation device 31 which forms a part of an introducer assembly 32 shown in FIGS. 4–6. The introducer assembly 32 is similar to that described in the U.S. Pat. No. 5,176,648 and as described therein comprises a radially extending flange 36 formed of a suitable material which is provided with an adhesive (not shown) to which there is secured a removable adhesive backing layer 37. A diaphragm 38 of reduced cross section is formed integral with flange 36 and adjoins an upstanding collar 39. The collar 39 is internally threaded and threadedly receives a clamping member in the form of a lock nut 41 which is provided with a radially extending knurled knob 42. The lower cylindrical extension 43 of the lock nut 41 is provided with an annular tapered surface 44 which is tapered downwardly and outwardly. The tapered surface 44 is adapted to engage the inclined surface 26 of the retaining ring 11 for compression of the same as hereinafter described. The lock nut 41 in conjunction with the retaining ring 11 forms the fixation device 31 for retaining a cannula 46 within the device.

Operation and use of the fixation device in conjunction with the introducer assembly 32 may now be briefly described as follows. The introducer assembly 32 as described in U.S. Pat. No. 5,176,648 can be placed on the abdomen of a patient in a position in which it is desired to make an opening into a cavity underlying the abdominal wall of the patient. The backing layer 37 can be stripped from the introducer assembly 32 and adhesive on the flange 36 is utilized to position the flange 36 with the adhesive thereon in the appropriate position on the abdomen to adhere to the skin of the patient. A cannula 46 with a conventional trocar (not shown) can be introduced through the fixation device 31 with the retaining ring 11 in an unclamped or relaxed position having the lock nut 41 in the raised position which can be accomplished by rotating the lock ring 42 in a counterclockwise direction so that the tapered surface 43 carried thereby is substantially out of engagement with the retaining ring 11. The retaining ring 11 in this position can accommodate cannulas of varying outside diameters.

The trocar (not shown) in the cannula is advanced to puncture the abdominal wall and is followed by the surgeon advancing the cannula 46 through the abdominal wall to form a seal with the skin of the patient. The cannula is advanced into the desired depth into the abdominal wall and then can be clamped in a fixed position by rotating of the lock nut 41 to cause the tapered surface 44 to first engage the inclined annular surface 26 and thereafter engage the outer surface 18 until the cannula 46 has been firmly gripped by the retaining ring 11.

The retaining ring 11 because of its unique construction firmly clamps the cannula 46 in the desired position. This is accomplished because of the circumferentially spaced-apart longitudinally extending indentations 21 provided in the wall 14 of the retaining ring 11. As explained previously, these indentations 21 do not interrupt the top or first end surface 16 of the retaining ring or the bottom or second end surface 17 of the retaining ring so that continuous edges are provided which surround the bore 13. This helps to ensure that the cannula will not catch on the edges as it is inserted through the retaining ring 11.

As can be seen in the drawings, the indentations 21 serve to create thin vertically extending wall portions in the wall 14 of the retaining ring which surrounds the bore 13 while the wall portions between the indentations 21 remain relatively thick. Thus, when the retaining ring 11 is forced into compression by threading of the lock nut 41 into the collar 39, the thin wall portions collapse under a buckling force forcing them outwardly into the bore and partially closing the V-shaped indentations 21 to reduce the included angle to create a series of circumferentially spaced-apart star-like protrusions or points 51 extending longitudinally of the bore 13 to partially occlude the bore 13 and to engage the outer surface of the cannula 46 as shown in FIG. 5. Further rotation of the lock ring 41 in a clockwise direction as viewed from the top side of the lock ring 41 causes further compression of the retaining ring 11 and causes greater compressive forces to be applied to the star-like protrusions or points 51 to cause firmer engagement of the cannula 46. Further rotation of the lock nut 41 causes a further and a complete closing of the V-shaped indentations 21 so that a substantially complete seal is formed around the outer surface of the cannula and with the retaining ring as shown in FIG. 6. In this position of the retaining ring 11, the cannula 46 is retained in a fixed longitudinal and rotational position within the fixation device 31 and in the introducer assembly 32.

When it is desired to release the cannula 46 it is merely necessary to rotate the lock nut 41 in a counterclockwise or opposite direction to release the cannula 46. As soon as the clamping forces are removed from the retaining ring 11 by retraction of the lock nut 41, the retaining ring assumes its original shape in which a smooth inner bore is provided to readily permit removal of the cannula 46.

In the collapse of the retaining ring 11 during the application of clamping forces thereto, the collapse is symmetric because of the equal spacing of the indentations around the circumference of the retaining ring. If such indentations were not present, there would be a tendency to have a nonsymmetric collapse of the wall 14 which would require much greater forces to create a cannula fixing engagement. The use of the indentations or notches 21 ensure that buckling failure of the retaining ring will occur in predetermined circumferentially spaced-apart regions as hereinbefore described.

With such a construction of the retaining ring 11, it has been found that it is very easy to provide retaining rings which will suitably clamp a cannula in which the outside diameters of the cannula can vary by at least as much as 0.060" which is approximately 1/16th of an inch. By utilizing a retaining ring 11 of the present invention in comparison to conventional retaining rings it has been found that there can be readily provided a three-fold increase in pull strength that is, the pulling force which is required to remove a cannula from the introducer assembly. Thus, the pull strength of 3-4 pounds can be readily achieved with the present invention which is more than adequate for fixedly retaining a cannula within an introducer assembly. The increased pulling forces which are obtained with the retaining ring 11 of the present invention are obtained by the greater frictional engagement created at the star-like protrusions or points 51 and the relative friction between the material for the retaining ring 11 and the cannula 46.

From the foregoing it can be seen that there has been provided a fixation device with a retaining ring therein which is capable of a large clamping range under low compressive loads. This has been accomplished without sacrificing a continuous edge surrounding the bore on either end of the retaining ring. The continuous edges provided for the bore inhibits catching of cannulas and the like which are inserted through the retaining ring. The continuous edge provided also facilitates the ability of the retaining ring to return to its original shape when the compressive load is removed. The use of the retaining ring in the present invention also makes it possible to make a fixation device which is less sensitive to durometer and material selection. It makes it possible to use higher durometer polymers while still maintaining large clamping ranges with low compressive force.

What is claimed is:

1. A retaining ring for use with a cannula fixation device to secure cannula of various sizes therein comprising a body of elastomeric material, said body having a generally cylindrical configuration and a longitudinal axis, said body also having an outer cylindrical surface and first and second end surfaces, said body having a bore extending therethrough along the longitudinal axis and through the first and second end surfaces with the body providing an inner cylindrical surface which defines the bore and a plurality of circumferentially spaced-apart indentations formed in the body and spaced from the inner cylindrical surface, the indentations extending parallel to the longitudinal axis and outwardly through the outer surface of the body between the first and second ends.

2. A retaining ring as in claim 1 wherein said indentations are substantially V-shaped in cross section.

3. A retaining ring as in claim 1 wherein said bore is cylindrical.

4. A retaining ring as in claim 1 wherein said body has an inclined annular surface extending from the first end surface to the outer cylindrical surface.

5. A retaining ring as in claim 4 wherein said inclined annular surface has an angle ranging from 25° to 55° with respect to the longitudinal axis of the body.

6. A retaining ring as in claim 4 wherein an additional inclined surface is formed in the body extending from the second end surface inwardly from the outer surface towards the bore.

7. A retaining ring as in claim 6 wherein said additional inclined surface has an angle ranging from 30° to 60° with respect to the longitudinal axis of the body.

8. A retaining ring as in claim 1 wherein said indentations gradually decrease in depth from the first end towards the second end.

9. A retaining ring as in claim 8 wherein said indentations have a slope ranging from 5° to 15°.

10. A fixation device for a cannula, comprising a collar having a bore extending therethrough, a retaining ring disposed in said bore in said collar and adapted to receive said cannula and a lock nut extending into said bore to compress said retaining ring, said retaining ring including a body of elastomeric material, said body having a wall with a generally cylindrical configuration having a longitudinal axis and having an outer cylindrical surface extending parallel to the longitudinal axis and having first and second end surfaces extending perpendicular to the longitudinal axis, said body having a bore defined by an inner cylindrical surface extending therethrough along the longitudinal axis and extending through the first and second end surfaces and a plurality of circumferentially spaced-apart indentations formed in the wall of the body and extending outwardly through the outer surface between the first and second ends, said body having an annular inclined surface extending from the first end surface to the outer cylindrical surface, said lock nut having a cylindrical extension with a bore extending therethrough, said cylindrical extension having an inclined surface for engaging the annular inclined surface of the retaining ring and the outer surface of the body to urge the retaining ring into compression as the lock nut is moved longitudinally with respect to the longitudinal axis of the body of elastomeric material.

11. A fixation device as in claim 10 together with an introducer assembly having a cannula for introduction into a cavity of a patient having skin overlying the cavity, the introducer assembly having a flange, said collar being carried by the flange and wherein said lock nut threadedly engages said collar during movement longitudinally of the body of the retaining ring, wherein said cannula extends through said lock nut and said retaining ring and wherein as said lock nut is moved to compress said retaining ring, said retaining ring collapses to form circumferentially spaced-apart star-like protrusions which engage the cannula to frictionally retain the cannula within the fixation device in a predetermined longitudinal and rotational position.

* * * * *

UNITED STATES PATENT AND TRADEMARK OFFICE
CERTIFICATE OF CORRECTION

PATENT NO. : 5,380,302

DATED : January 10, 1995

INVENTOR(S) : Michael J. Orth

It is certified that error appears in the above-indentified patent and that said Letters Patent is hereby corrected as shown below:

In the Title: at [54], delete "IDENTATIONS" and insert therefor --INDENTATIONS--.

Signed and Sealed this

Seventh Day of November, 1995

Attest:

BRUCE LEHMAN

*Attesting Officer*    *Commissioner of Patents and Trademarks*